US010478505B2

(12) United States Patent
Rogawski (10) Patent No.: US 10,478,505 B2
(45) Date of Patent: Nov. 19, 2019

(54) EDIBLE OILS TO ENHANCE DELIVERY OF ORALLY ADMINISTERED STEROIDS

(71) Applicant: The Regents of the University of California, Oakland, CA (US)

(72) Inventor: Michael A. Rogawski, Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 27 days.

(21) Appl. No.: 14/345,385

(22) PCT Filed: Sep. 21, 2012

(86) PCT No.: PCT/US2012/056509
§ 371 (c)(1),
(2) Date: Mar. 17, 2014

(87) PCT Pub. No.: WO2013/043985
PCT Pub. Date: Mar. 28, 2013

(65) Prior Publication Data
US 2014/0343027 A1    Nov. 20, 2014

Related U.S. Application Data

(60) Provisional application No. 61/538,546, filed on Sep. 23, 2011.

(51) Int. Cl.
A61K 47/46    (2006.01)
A61K 31/57    (2006.01)
A61K 47/44    (2017.01)
A61K 9/48     (2006.01)

(52) U.S. Cl.
CPC ............ A61K 47/46 (2013.01); A61K 9/4816 (2013.01); A61K 9/4833 (2013.01); A61K 9/4858 (2013.01); A61K 31/57 (2013.01); A61K 47/44 (2013.01)

(58) Field of Classification Search
CPC ..................................................... A61K 47/46
USPC ...................................................... 514/179
See application file for complete search history.

(56) References Cited

U.S. PATENT DOCUMENTS

| | | | |
|---|---|---|---|
| 3,865,939 A * | 2/1975 | Jandacek ................. 514/182 |
| 5,719,197 A | 2/1998 | Kanios et al. | |
| 6,245,757 B1 | 6/2001 | Chopp et al. | |
| 6,455,516 B1 | 9/2002 | Backstrom et al. | |
| 6,780,853 B1 | 8/2004 | Upasani et al. | |
| 7,060,255 B2 | 6/2006 | Rabinowitz et al. | |
| 7,064,116 B2 | 6/2006 | Calogeropoulou et al. | |
| 7,090,830 B2 | 8/2006 | Hale et al. | |
| 7,630,757 B2 | 12/2009 | Dorfmeister et al. | |
| 7,816,074 B2 | 10/2010 | Smith et al. | |
| 7,858,609 B2 | 12/2010 | Shaw et al. | |
| 8,012,958 B2 | 9/2011 | Sabnani et al. | |
| 8,697,678 B2 | 4/2014 | Goodchild et al. | |
| 9,084,797 B2 | 7/2015 | Caufriez et al. | |
| 2002/0072509 A1 | 6/2002 | Stein et al. | |
| 2003/0032638 A1 | 2/2003 | Kim et al. | |
| 2006/0063707 A1 | 3/2006 | Baudry et al. | |
| 2006/0198896 A1 | 9/2006 | Liversidge et al. | |
| 2007/0081948 A1 | 4/2007 | Morton | |
| 2007/0287931 A1 | 12/2007 | Dilorenzo | |
| 2008/0269183 A1 | 10/2008 | Mellon et al. | |
| 2009/0074677 A1 | 3/2009 | Marx et al. | |
| 2009/0130216 A1 | 5/2009 | Cartt et al. | |
| 2009/0162441 A1 | 6/2009 | Bartus et al. | |
| 2009/0198145 A1 | 8/2009 | Chow | |
| 2009/0203658 A1 | 8/2009 | Marx et al. | |
| 2009/0221544 A1 | 9/2009 | Stein et al. | |
| 2009/0239942 A1 | 9/2009 | Cloyd | |
| 2009/0325920 A1 | 12/2009 | Hoffman et al. | |
| 2010/0136105 A1* | 6/2010 | Chen ................... A61K 47/22 424/455 |
| 2010/0234335 A1* | 9/2010 | Gravanis ................ C07J 21/00 514/173 |
| 2010/0297181 A1 | 11/2010 | Hanada et al. | |
| 2010/0316678 A1 | 12/2010 | Goodchild | |
| 2011/0054038 A1 | 3/2011 | Glozman | |
| 2011/0306579 A1 | 12/2011 | Stein | |
| 2011/0319386 A1 | 12/2011 | Barlow et al. | |
| 2012/0302535 A1 | 11/2012 | Caufriez et al. | |
| 2013/0309306 A1 | 11/2013 | Rogawski et al. | |
| 2014/0050789 A1 | 2/2014 | Rogawski et al. | |

(Continued)

FOREIGN PATENT DOCUMENTS

CA    2 443 466 A1    12/2002
EP    0 233 849 A1    1/1987

(Continued)

OTHER PUBLICATIONS

Frye the neurosteroid 3-alpha 5 alpha-THP has antiseizure and possible neuroprotective effects in an animal model of epilepsy. (Brain Research (1995) vol. 696, pp. 113-120).*
PubChem CID 92786. [online] Retrieved on Dec. 7, 2015 <url:https://pubchem.ncbi.nlm.nih.gov/compound/92786#section=Top>.*
Burdock, G.A. "Encyclopedia of Food Additives and Coloring, vol. 3" Taylor & Francis (1997) pp. 2412.*
Haut et al. Epilepsia (2002) vol. 43 pp. 711-715.*
Kaminski et al. Epilepsia (2004) vol. 45, pp. 864-867.*
Weisberg et al. (Essentials of Clinical Neurology: Chapter 11 (1983) pp. 167-194.*
U.S. Office Action dated Apr. 16, 2015 issued in U.S. Appl. No. 13/885,660.
U.S. Office Action dated Jun. 12, 2015 issued in U.S. Appl. No. 13/964,922.

(Continued)

*Primary Examiner* — Savitha M Rao
*Assistant Examiner* — Taina D Matos Negron
(74) *Attorney, Agent, or Firm* — Squire Patton Boggs (US) LLP (57) ABSTRACT

The present invention relates to the formulation of steroids, including neurosteroids (e.g., allopregnanolone (ALP)) in edible oils to enhance their absorption when administered, e.g., orally or transmucosally to a patient.

16 Claims, 7 Drawing Sheets

(56) References Cited

U.S. PATENT DOCUMENTS

| | | |
|---|---|---|
| 2014/0057885 A1 | 2/2014 | Reddy et al. |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0313915 A1 | 11/2015 | Rogawski et al. |

FOREIGN PATENT DOCUMENTS

| | | | |
|---|---|---|---|
| EP | 0 808 325 A1 | | 11/1997 |
| JP | 2009-524582 A | | 7/2009 |
| JP | 2015-513316 A | | 5/2015 |
| WO | WO 91/11172 A1 | | 8/1991 |
| WO | WO 93/03732 A1 | | 3/1993 |
| WO | WO 95/21617 A1 | | 8/1995 |
| WO | WO 96/16076 A1 | | 5/1996 |
| WO | WO 97/03677 A1 | | 2/1997 |
| WO | WO 99/45931 A1 | | 9/1999 |
| WO | WO 02/30409 A2 | | 4/2002 |
| WO | WO 2004/019953 A1 | | 3/2004 |
| WO | WO 2006/102644 A2 | | 9/2006 |
| WO | WO 2007/062266 | | 5/2007 |
| WO | WO 2008/157460 | | 12/2008 |
| WO | WO 2010/042925 A2 | | 4/2010 |
| WO | WO 2010/063030 A2 | | 6/2010 |
| WO | WO 2010/107815 | | 9/2010 |
| WO | WO 2011/088503 | | 7/2011 |
| WO | WO 2012/059456 A1 | | 5/2012 |
| WO | WO 2012/075286 | | 6/2012 |
| WO | WO 2013/043985 | | 3/2013 |
| WO | WO 2013/112605 | | 8/2013 |
| WO | WO 2014/028398 | | 2/2014 |
| WO | WO 2014/031792 A2 | | 2/2014 |
| WO | WO 2014/085668 | | 6/2014 |
| WO | WO 2014/108808 A2 | | 7/2014 |

OTHER PUBLICATIONS

PCT International Search Report (Declaration of non-establishment of International Search Report) and Written Opinion dated Jun. 15, 2012 issued in PCT/US2011/062888.
PCT International Preliminary Report on Patentability and Written Opinion dated Jun. 13, 2013 issued in PCT/US2011/062888.
PCT International Search Report and Written Opinion dated Dec. 27, 2012 issued in PCT/US2012/056509.
PCT International Preliminary Report on Patentability and Written Opinion dated Apr. 3, 2014 issued in PCT/US2012/056509.
PCT International Search Report and Written Opinion dated Jan. 13, 2014 issued in PCT/US2013/054562.
PCT International Preliminary Report on Patentability and Written Opinion dated Jun. 18, 2015 issued in PCT/US2013/054562.
PCT International Search Report and Written Opinion dated Mar. 17, 2014 issued in PCT/US2013/072351.
PCT International Preliminary Report on Patentability and Written Opinion dated Jun. 11, 2015 issued in PCT/US2013/072351.
Bancaud, Jean; Henriksen, Olaf; Rubio-Donnadieu, Francisco; Seino (Shizuoka), Masakatsu; Dreifuss, Fritz E.; Penry, J. Kiffin; (From the Commission on Classification and Terminology of the International League Against Epilepsy) (Aug. 1981) "Proposal for Revised Clinical and Electroencephalographic Classification of Epileptic Seizures," *Epilepsia*, 22:489-501.
Bobb et al. "Allopregnanolone to Treat Refractory Status Epilepticus," *presented at American Clinical Neurophysiology Society (ACNS) Annual Meeting & Courses*, The Westin Peachtree Plaza, Atlanta, Georgia, (Feb. 4-9, 2014) Abstract S26.
Broomall et al. (Dec. 2014) "Pediatric Super-Refractory Status Epilipticus Treated with Allopregnanolone," *Ann. Neurol*, 76:911-915.
Brunn et al. (2015) "Combined treatment with diazepam and allopregnanolone reverses tetramethylenedisulfotetramine (TETS)-induced calcium dysregulation in cultured neurons and protects TETS-intoxicated mice against lethal seizures," *Neuropharmacology*, 95:332-342.
Cao et al. (2012) "Tetramethylenedisulfotetramine Alters $Ca^{2+}$ Dynamics in Cultured Hippocampal Neurons: Mitigation by NMDA Receptor Blockade and $GABA_A$ Receptor-Positive Modulation," *Toxicological Sciences*, 130(2):362-372.
Dhir et al. (Jan. 2011) "Seizure Protection by Intrapulmonary Delivery of Propofol Hemisuccinate," *The Journal of Pharmacology and Experimental Therapeutics*, 336(1):215-222.
Dhir et al. (2012) "Role of neurosteroids in the anticonvulsant activity of midazolam," *British Journal of Pharmacology*,165(8):2684-2691.
Dhir et al. (2013) "Seizure protection by intrapulmonary delivery of midazolam in mice," *Neuropharmacology*, 73:425e431.
Galvin et al. (1987) "Midazolam: an effective intravenous agent for seizure control," *Archives of emergency medicine*, 4:169-172.
Gasior et al. (1997) "Anticonvulsant and Behavioral Effects of Neuroactive Steroids Alone and in Conjunction with Diazepam[1]," *The Journal of Pharmacology and Experimental Therapeutics, The American Society for Pharmacology and Experimental Therapeutics*, 282(2):543-553.
Gül et al. (2006) "Sterols and the phytosterol content in oilseed rape (*Brassica napus* L.)," *Journal of Cell and Molecular Biology*, 5:71-79.
Hanley et al. (1998) "Use of Midazolam in the treatment of refractory status epilepticus," *Clinical Therapeutics*, 20(6):1093-1105.
Haut, Sheryl R. (2006) "Seizure clustering," *Epilepsy & Behavior*, 8:50-55.
Kanto (May/Jun. 1985) Midazolam: The First Water-soluble Benzodiazepine Pharmacology, Pharmacokinetics and Efficacy in Insomnia and Anesthesia, *Pharmacotherapy*, 5(3):138-155.
Martini et al. (2000) "Nasal and pulmonary drug delivery systems," *Exp. Opin. Ther. Patents*, 10(3):315-323.
Nanjwade et al. (Sep.-Oct. 2011) "Pulmonary Drug Delivery: Novel Pharmaceutical Technologies Breathe New Life into the Lungs," *PDA J Pharm Sci and Tech*, [Downloaded from journal.pda.org on Oct. 8, 2015] 65:513-534.
Oka et al. (2006) "A Reliable Method for Intratracheal Instillation of Materials to the Entire Lung in Rats," *J Toxicol Pathol*, 19:107-109.
Pires et al. (2009) "Intranasal Drug Delivery: How, Why and What for?" *J Pharm Pharmaceut Sci*, 12(3):288-311.
Ramsay, Eugene R., (1993) "Treatment of Status Epilepticus," *Epilepsia*, 34(Suppl. 1):571-581.
Reddy (Sep. 2013) " SGE-102: a novel therapy for refractory status epilepticus," *Epilepsia*, Abstract, 54 Supp16:81-83, 2 pages [retrieved on Sep. 7, 2015 at http://www.ncbi.nlm.nih.gov/pubmed/24001082].
Rogawski et al. (Sep. 2013) "Neuroactive Steroids for the Treatment of Status Epilepticus," *Epilepsia*, Author manuscript; available in PMC Sep. 1, 2014, 54(0 6): 93-98, doi:10.1111/epi.12289.
Sanborn et al. (May 28, 2002) "Identifying and managing adverse environmental health effects: 4. Pesticides," *CMAJ*, 166(11):1431-1436.
Vaitkevicius et al. (2013) "Successful Allopregnanolone Treatment of New Onset Refractory Status Epilepticus (Norse) Syndrome: First in Man Experience," *Epilepsia*, Abstract, P29, p. 114.
U.S. Final Office Action dated Nov. 30, 2015 issued in U.S. Appl. No. 13/885,660.
U.S. Final Office Action dated Apr. 14, 2016 issued in U.S. Appl. No. 13/964,922.
U.S. Restriction Requirement dated May 9, 2016 issued in U.S. Appl. No. 14/646,886.
European Extended Search Report dated May 2, 2016 issued in Application No. EP 13 85 7993.
European Office Action dated Apr. 5, 2017 issued in Application No. EP 13 85 7993.3.
U.S. Office Action dated Feb. 22, 2017 issued in U.S. Appl. No. 13/885,660.
U.S. Office Action dated Jan. 19, 2017 issued in U.S. Appl. No. 13/964,922.
U.S. Office Action dated Jan. 4, 2017 issued in U.S. Appl. No. 14/646,886.

(56) References Cited

OTHER PUBLICATIONS

Haut et al. (2015) "Seizure clusters: characteristics and treatment." *Curr Opin Neurol.* 28(2), abstract only.

Lossin et al. (2012) "Allopregnanolone Treatment in a Rat Pediatric Status Epilepticus Model: Comparison With Diazepam," *American Epilepsy Society*,(Abst. 3.220) [retrieved on Nov. 29, 2012 from http://www.aesnet.org/go/publications/aes-abstracts/abstract-search/mode/display/st/roga . . . ], 1 page.

Zolkowska et al. (2012) "Anticonvulsant Activity of Intravenous and Intramuscular Allopregnenalone,"*American Epilepsy Society*,(Abst. 1.023) [retrieved on Nov. 29, 2012 from http://www.aesnet.org/go/publications/aes-abstracts/abstract-search/mode/display/st/roga . . . ], 1 page.

Zolkowska et al. (2012) "Anticonvulsant Activity of Intravenous and Intramuscular Allopregnenalone," *American Epilepsy Society*, (Poster), UC Davis, University of California, 1 page.

Botella, et al., "Neuroactive Steroids. 1. Positive Allosteric Modulators of the (γ-Aminobutyric Acid) A Receptor: Structure—Activity Relationships of Heterocyclic Substitution at C-21" *Journal of Medicinal Chemistry* 58:3500-3511, 2015.

Carrin, et al., "Peanut oil: Compositional data" *Eur. J. Lipid Sci. Technol.* 112:697-707, 2010.

Kanes, et al., "Open-label, proof-of-concept study of brexanolone in the treatment of severe postpartum depression" *Hum Psychopharmacol Clin Exp.* 32:e2576, pp. 1-6, 2017.

Kanes, et al., "Brexanolone (SAGE-547 injection) in post-partum depression: a randomised controlled trial" www.thelancet.com, Jun. 12, 2017.

Monaghan, et al., "Initial Human Experience with Ganaxolone, a Neuroactive Steroid with Antiepileptic Activity" *Epilepsia* 38(9):1026-1031, 1997.

Przybylski, R, Mag T, Eskin Nam, Mc Donald BE (2005) Canola Oil. In: Shahidi F (ed) Bailey's industrial oil and fat products. 6th edn. Wiley-Interscience, Hoboken, pp. 61-122.

Przybylski, Dr. Roman, "Canola Oil: Physical and Chemical Properties," undated brochure.

Wang, et al., "Open-Label Allopregnanolone Treatment of Men with Fragile X-Associated Tremor/Ataxia Syndrome" *Neurotherapeutics* pp. 1-11, 2017.

"Rat and Mice Weights" *Animal Resources Centre* http://www.arc.wa.gov.au/?page_id=125, retrieved Jan. 28, 2018.

"Migyol® 810, 812, INCI: Caprylic/ Capric Triglyceride, Nongreasy emollient" Cremer Care, brochure, Mar. 2013.

"Neobee® Medium Chain Triglycerides" Stepan Lipid Nutrition, undated brochure.

U.S. Final Office Action dated Oct. 20, 2017 issued in U.S. Appl. No. 13/885,660.

U.S. Restriction Requirement dated Apr. 6, 2015 issued in U.S. Appl. No. 14/374,080.

U.S. Office Action dated Nov. 2, 2015 issued in U.S. Appl. No. 14/374,080.

U.S. Final Office Action dated Jun. 14, 2016 issued in U.S. Appl. No. 14/374,080.

U.S. Restriction Requirement dated Oct. 8, 2015 issued in U.S. Appl. No. 13/972,851.

U.S. Restriction Requirement dated Mar. 7, 2016 issued in U.S. Appl. No. 13/972,851.

U.S. Restriction Requirement dated Feb. 6, 2015 issued in U.S. Appl. No. 13/972,851.

U.S. Office Action dated Jun. 24, 2016 issued in U.S. Appl. No. 13/972,851.

U.S. Final Office Action dated Mar. 31, 2017 issued in U.S. Appl. No. 13/972,851.

Australian Examination report No. 1 dated Jul. 27, 2017 issued in Application No. AU 2013352141.

Japanese Office Action dated Jul. 19, 2017 issued in Application No. JP 2015-545458.

PCT International Search Report and Written Opinion dated Mar. 27, 2013 issued in Application No. PCT/US2013/022772.

PCT International Preliminary Report on Patentability and Written Opinion dated Dec. 31, 2014 issued in Application No. PCT/US2013/022772.

European Extended Search Report dated Jan. 14, 2016 issued in Application No. EP 13 740 743.3.

European Examination Report dated Mar. 2, 2017 issued in Application No. EP 13 740 743.3.

PCT International Search Report and Written Opinion dated Jan. 29, 2014 issued in Application No. PCT/US2013/056062.

PCT International Preliminary Report on Patentability and Written Opinion dated Feb. 24, 2015 issued in Application No. PCT/US2013/056062.

European Extended Search Report dated Jan. 12, 2016 issued in Application No. EP 13 830 765.7.

Aladdin et al. (2008) "Refractory Status Epilepticus During Pregnancy Secondary to Cavernous Angiona," Epilepsia, 49(9):1627-1629.

Allen et al. (2013) "Menstrual Phase, Depressive Symptoms, and Allopregnanolone During Short-Term Smoking Cessation," Experimental and Clinical Psychopharmacology, 21(6):427-433.

"Allopregnanolone for the Treatment of Traumatic Brain Injury," Clinical Trials.gov, [Updated May 22, 2013], pp. 1-4.

Anderson et al. (2014) "Oxidative/Nitrosative Stress and Immunoinflammatory Pathways in Depression: Treatment Implications," Current Pharmaceutical Design, 20(25):4126-4161.

Bali et al. (2014) "Multifunctional aspects of allopregnanolone in stress and related disorders," Progress in Neuro-Psychopharmacology & Biological Psychiatry, 48:64-78.

Beckley et al. (2011) "Progesterone receptor antagonist CDB-4124 increases depression-like behavior in mice without affecting locomotor ability," Psychoneuroendocrinology, 36:824-833.

Biagini et al. (2006) "Endogenous neurosteroids modulate epileptogenesis in a model of temporal lobe epilepsy," Experimental Neurology, 201:519-524.

Bleck et al. (2005) "Refractory Status Epileptics" Current Opinion in Critical Care, 11:117-120.

Brown et al. (2014) "A Randomized, Double-Blind, Placebo-Controlled Trial of Pregnenolone for Bipolar Depression," Neuropsychopharmacology, 39:2867-2873.

Carta et al. (2012) "GABAergic neuroactive steroids: a new frontier in bipolar disorders?," Behavioral and Brain Functions, 8:61, 8pp.

Chen et al. (1996) "Ibogaine Block of the NMDA Receptor: In Vitro and In Vivo Studies," Neuropharmacology, 35(4):423-431.

Chiasari et al. (2009) "The Influence of Neuroactive Steroid Lipophilicity on GABA Receptor Modulation: Evidence for a Low-Affinity Interaction," Journal of Neurophysiology, 102:1254-1264.

Claassen et al. (2002) "Treatment of Refractory Status Epilepticus with Pentobarbital, Propofol, or Midazolam: A Systematic Review," Epilepsia, 43(2):146-153.

Deligiannidis et al. (2013) "GABAergic neuroactive steroids and resting-state functional connectivity in postpartum depression: A preliminary study," Journal of Psychiatric Research, 47:816-828.

Deligiannidis et al. (2016) "Peripartum neuroactive steroid and γ-aminobutyric acid profiles in women at-risk for postpartum depression," Psychoneuroendocrinology, Accepted Manuscript, [http://dx.doi.org/10.1016/j.psyneuen.2016.05.010], 33pp.

Delorenzo et al. (1995) "Epidemiology of Status Epilepticus," Journal of Clinical Neurophysiology, 12(4):316-325.

Deutsch et al. (1996) "Evaluation of in Vivo Interactions in Mice Between Flurazepam and Two Neuroactive Steroids," Pharmacology Biochemistry & Behavior, 55(3):323-326.

D'Aquila et al. (2010) "Dopamine is involved in the antidepressant-like effect of allopregnanolone in the forced swimming test in female rats," Behavioural Pharmacology, 21:21-28.

Drugan et al. (Feb. 2013) "Resilience in shock and swim stress models of depression," frontiers in Behavioral Neuroscience, 7(14):8pp.

Eser et al. (2006) "Neuroactive Steroids in Depression and Anxiety Disorders: Clinical Studies," Neuroendocrinology, 84:244-254.

Eser et al. (2006) "Neuropsychopharmacological properties of neuroactive steroids in depression and anxiety disorders" Psychopharmacology, 186:373-387.

(56) References Cited

OTHER PUBLICATIONS

Evans et al. (2012) "Allopregnanolone regulates neurogenesis and depressive/anxiety-like behaviour in a social isolation rodent model of chronic stress," Neuropharmacology, 63:1315-1326.
Finn et al. (1994) "The Estrus Cycle, Sensitivity to Convulsants and the Anticonvulsant Effect of Neuroactive Steroid," The Journal of Pharmacology and Experimental Therapeutics, 271:164-170.
Frye et al. (2000) "Infusion of 3a,5a-THP to the pontine reticular formation attenuates PTZ-induced seizures," Brain Research, 881:98-102.
Frye et al. (2012) "Effects and mechanisms of 3α, 5α,-THP on emotion, motivation, and reward functions involving pregnane xenobiotic receptor," Frontiers in Neuroscience, 5(136):18pp.
Haas et al. (1992) "Ketamine: A Review of Its Pharmacologic Properties and Use in Ambulatory Anesthesia," Anesthesia, Anesthesia Progress, The American Dental Society of Anesthesiology, 39:61-68.
He et al. (Jan. 2000) "862.4: Allopregnanolone facilitates spatial learning after traumatic brain injury," Abstracts of the Annual Meeting of the Society for Neuroscience; 30th Annual Meeting of the Society of Neuroscience, Society for Neuroscience, Washington, DC, US; New Orleans, LA, USA, 26:2296.
Hellgren et al. (2014) "Low Serum Allopregnanolone Is Associated with Symptoms of Depression in Late Pregnancy," Neuropsychobiology, 69:147-153.
Hincal (2005) "Recent advances in drug delivery using amphiphilic cyclodextrin nanoparticles," European Journal of Pharmaceutical Sciences, 23S1:S3-S4.
Hunter et al. (Mar. 2012) "Status Epilepticus: A Review, With Emphasis on Refractory Cases," Canadian Journal of Neurological Sciences, 39(2):157-169.
Jain et al. (2001) "Hygroscopicity, phase solubility and dissolution of various substituted sulfobutylether b-cyclodextrins (SBE) and danazol-SBE inclusion complexes," International Journal of Pharmaceutics, 212:177-186.
Kask et al. (2008) "Allopregnanolone impairs episodic memory in healthy women," Psycopharmacology, 199:161-168.
Kask et al. (2009) "Allopregnanolone has no effect on startle response and prepulse inhibition of startle response in patients 16 with premenstrual dysphoric disorder or healthy controls," Pharmacology, Biochemistry and Behavior, 92:608-613.
Khanna et al., (2015) "Nanotoxicity: An Interplay of Oxidative Stress, Inflammation and Cell Death," Nanomaterials, 5:1163-1180.
Kim et al. (2011) "Modulation of presynaptic GABAA receptors by endogenous neurosteroids," British Journal of Pharmacology, 164:1698-1710.
Kimmel et al. (2016) "Oxytocin receptor DNA methylation in postpartum depression," Psychoneuroendocrinology, 69:150-160.
Kokate et al. (1994) "Anticonvulsant Activity of Neurosteroids: Correlation with g-Aminobutyric Acid-Evoked Chloride Current Potentiation," The Journal of Pharmacology and Experimental Therapeutics, 270(3):1223-1229.
Kokate et al., (1996) "Neuroactive Steroids Protect Against Pilocarpine- and Kainic Acid-induced Limbic Seizures and Status Epilepticus in Mice," Neuropharmacology, 35(8):1049-1056.
Kokate et al. (1999) "Convulsant actions of the neurosteroid pregnenolone sulfate in mice," Brain Research, 831:119-124.
Kramer (2012) "Early Ketamine to Treat Refractory Status Epilepticus," Neurocrit. Care, 16:299-305.
Lahiani-Skiba et al. (2005) "Solubility and Dissolution Rate of Progesterone-Cyclodextrin-Polymer Systems," Drug Development and Industrial Pharmacy, 32(9):1043-1058.
Larsen et al. (2005) "Phase Solubility and Structure of the Inclusion Complexes of Prednisolone and 6a-Methyl Prednisolone with Various Cyclodextrins," Journal of Pharmaceutical Sciences, 94(3):507-515.
Leroy et al. (2004) "Pharmacological plasticity of GABAA receptors at dentate gyrus synapses in a rat model of temporal lobe epilepsy," J. Physol., 557(2):473-487.

Li et al., (Sep. 2010) "Nanoparticle-induced pulmonary toxicity," Experimental Biology and Medicine, 235:1025-1033.
Lonsdale et al. (2007) "The Anticonvulsant effects of allopregnanolone against amygdala-kindled seizures in female rats," Neuroscience Letters, 411:147-151.
Madl et al. (2014) "Nanoparticles, Lung Injury, and the Role of Oxidant Stress," Annu Rev Physiol., 76:447-465.
Maguire et al. (Jul. 31, 2008) "GABAAR Plasticity during Pregnancy Relevance to Postpartum Depression," Neuron, 59:207-213.
Masson et al. (2007) "Cyclodextrins and the liquid-liquid phase distribution of progesterone, estrone and prednicarbate," J Incl Phenom Macrocycl Chem, 57:481-487.
Mayer et al. (2002) "Refractory Status Epilepticus Frequency, Risk Factors, and Impact on Outcome," Archives of Neurology, 59:205-210.
Meierkord et al. (2010) "EFNS Guideline on the Management of Status Epilepticus in Adults" European Journal of Neurology, 17:348-355.
Merzlikine et al. (2011) "Development of machine learning models of b-cyclodextrin and sulfobutylether-b-cyclodextrin complexation free energies," International Journal of Pharmaceutics, 418:207-216.
"Midazolam Hydrochloride—midazolam hydrochloride injection, solution," Ebewe Parenta (TM) Pharmaceuticals, Inc., revised 2006, 34pp [Downloaded on Oct. 18, 2017 at file:///C:Users/mhaghighatian/Documents/e-Red%20Folder/13885660New%20folder%2 . . . ].
Monagle et al. (2015) "A Phase 1c Trial Comparing the Efficacy and Safety of a New Aqueous Formulation of Alphaxalone with Propofol," Anesthesia & Analgesia, 121(4):914-924.
Munari et al. (1979) "The Use of Althesin in Drug-Resistant Status Epilepticus," Epilepsia, 20:475-484.
Murayama et al. (2006) "Effects of neurosteroid 3a-hydroxy-5apregnan-20-one on ethanol-mediated paired-pulse depression of population spikes in the CA1 region of rat hippocampal slices," Neuroscience Letters, 394:28-32.
Nappi et al. (Jan. 2001) "Serum Allopregnanolone in Women With Postpartum "Blues"," Obstetrics & Gynecology, 97(1):77-80.
Nin et al. (2012) "The effect of intra-nucleus accumbens administration of allopregnanolone on δ and γ2 GABAA receptor subunit mRNA expression in the hippocampus and on depressive-like and grooming behaviors in rats," Pharmacology, Biochemistry and Behavior, 103:359-366.
Novy et al. (2010) "Refractory Status Epilepticus: A Prospective Observational Study," Epilepsia, 51(2):251-256.
Osborne et al. (2015) "Replication of Epigenetic Postpartum Depression Biomarkers and Variation with Hormone Levels," Neuropsychopharmacology, accepted article preview Oct. 27, 2015; Accepted Manuscript, [doi: 10.1038/npp.2015.333], 32pp.
Park et al. (2011) "Multiple effects of allopregnanolone on GABAergic responses in single hippocampal CA3 pyramidal neurons," European Journal of Pharmacology, 652:46-54.
Pieribone et al. (2007) "Clinical Evaluation of Ganaxolone in Pediatric and Adolescent Patients with Refractory Epilepsy," Epilepsia, 48(10):1870-1874.
Puia et al. (Nov. 2012) "Novel modulatory effects of neurosteroids and benzodiazepines on excitatory and inhibitory neurons excitability: a multi-electrode array recording study," Frontiers in Neural Circuits, 6(94):17pp.
Reddy (Oct. 2011) "Role of anticonvulsant and antiepileptogenic neurosteroids in the pathophysiology and treatment of epilepsy," Frontiers in Endocrinology, 2:38,11pp [Published online Oct. 5, 2011, doi: 10.3389/fendo.2011.00038; Pre-published online Aug. 9, 2011].
Reddy et al. (2012) "Neurosteroids—Endogenous Regulators of Seizure Susceptibility and Role in Treatment of Epilepsy," Jasper's Basic Mechanisms of the Epilepsies Fourth Edition, pp. 1-23.
Rosenthal et al. (2017) "Brexanolone as Adjunctive Therapy in Super-Refractory Status Epilepticus," Annals of Neurology, John Wiley & Sons, [Accepted Article, doi: 10. 1002/ana.25008] 32pp.
Rosseti et al. (2011) "A Randomized Trial for the Treatment of Refractory Status Epilepticus," Neurocritical Care Society, 14(1):4-10.

(56) References Cited

OTHER PUBLICATIONS

Saady et al. (1979) "Case Report: Althesin in Status Epilepticus," Aneasth. Intens. Care, 7(3):267-270.
Sahin et al. (2001) "Outcome of Severe Refractory Status Epilepticus in Children," Epilepsia, 41(11):1461-1467.
Santoru et al. (2014) "Decreased allopregnanolone induced by hormonal contraceptives is associated with a reduction in social behavior and sexual motivation in female rats," Psychopharmacology, 14pp.
Schiller et al. (2014) "Allopregnanolone as a mediator of affective switching in reproductive mood disorders," Psychopharmacology, 11pp.
Schiller et al. (2015) "The role of reproductive hormones in postpartum depression," CNS Spectrums, 20(1):48-59.
Schüle et al. (2011) "Neuroactive Steroids in Affective Disorders: Target for Novel Antidepressant or Anxiolytic Drugs?," Neuroscience, 191:55-77.
Schüle et al. (2014) "The role of allopregnanolone in depression and anxiety," Progress in Neurobiology, 113:79-87.
Shah et al. (2001) "Peripheral WBC Count and Serum Prolactin Level in Various Seizure Types and Nonepileptic Events," Epilepsia, 42(11):1472-1475.
Shimizu et al. (2015) "Allopregnanolone Increases Mature Excitatory Synapses Along Dendrites Via Protein Kinase a Signaling," Neuroscience, 305:139-145.
Shorvon et al. (2007) "The Proceedings of the First London Colloquium on Status Epilepticus—University College London, Apr. 12-15, 2007," Epilepsia, 48(8):1-3.
Shorvon et al., (Oct. 2011) "The treatment of super-refractory status epilepticus: a critical review of available therapies and a clinical treatment protocol," Brain, A Journal of Neurology, 134(Pt 10):2802-2818 [Epub. Sep. 13, 2011].
Shorvon et al. (2012) "The Outcome of Therapies in Refractory and Super-Refractory Convulsive Status Epilepticus and Recommendations for Therapy," Brain, 135(8):2134-2328.
Smith et al. (2013) "The Influence of Stress At Puberty on Mood and Learning: Role of the $\alpha 4\beta\delta$ GABAA Receptor," Neuroscience, 249:192-213.
Timby et al. (2006) "Pharmacokinetic and behavioral effects of allopregnanolone in healthy women," Psycopharmacology, 186(3):414-424.
Timby et al. (2016) "Women with premenstrual dysphoric disorder have altered sensitivity to allopregnanolone over the menstrual cycle compared to controls—a pilot study," Psychopharmacology, 233:2109-2117.
Tolmacheva et al. (2007) "The role of ovarian steroid hormones in the regulation of basal and stress induced absence seizures," Journal of Steroid Biochemistry & Molecular Biology, 104:281-288.
Tongiani et al. (2009) "Sulfobutyl Ether-Alkyl Ether Mixed Cyclodextrin Derivatives With Enhanced Inclusion Ability," Journal of Pharmaceutical Sciences, 98(12):4769-4780.
Turkmen et al. (2011) "Tolerance to Allopregnanolone with Focus on the GABA-A Receptor," British Journal of Pharmacology, 162:311-327.
Ueda et al. (2008) "Evaluation of a Sulfobutyl Ether b-Cyclodextrin as a Aolubilizing/Stabilizing Agent for Several Drugs," Drug Development and Industrial Pharmacy, 24(9):863-867.
Vaitkevicius et al. (2017) "First-in-man allopregnanolone use in super-refractory status epilepticus," Annals of Clinical and Translational Neurology, 4(6):411-414 [doi: 10.1002/acn3.408].
Vanlandingham et al. (2008) "Progesterone and its metabolite allopregnanolone differentially regulate hemostatic proteins after traumatic brain injury," Journal of Cerebral Blood Flow & Metabolism, 28:1786-1794.
Zhu et al. (2001) "Evaluation and comparison of the pharmacokinetic and pharmacodynamic properties of allopregnanolone and pregnanolone at induction of anaesthesia in the male rat," British Journal of Anaesthesia, 86(3):403-412.
Zia et al. (1996) "Effect of Alkyl Chain and Degree of Substitution on the Complexation of Sulfoalkyl Ether b-Cyclodextrins with Steroids," Journal of Pharmaceutical Sciences, 86(2):220-224.
Zia et al. (2000) "Thermodynamics of Binding of Neutral Molecules to Sulfobutyl Ether b-Cyclodextrins (SBE-b-CDs): The Effect of Total Degree of Substitution," Pharmaceutical Research, 17(8):936-941.
Zia et al. (2001) "Effect of Cyclodextrin Charge on Complexation of Neutral and Charged Substrates: Comparison of (SBE) 7M-b-CD to HP-b-CD," Pharmaceutical Research, 18(5):667-673.
Zolkowska et al. (2012) "Anticonvulsant Activity of Intravenous and Intramuscular Allopregnenalone," 125. 26a-30a. 26b-30b. American Epilepsy Society: 2012 Annual Meeting Abstracts. Dec. 1, 2012. 31-42. [URL:http://www.grupio.com/events_2/session.php?id=392260&event_id=327&track=Poster+Session+1)]; p. 1.
U.S. Appl. No. 15/632,360, filed Jun. 25, 2017, Rogawski et al.
U.S. Appl. No. 15/649,460, filed Jul. 13, 2017, Rogawski et al.
Griffin, Lisa D., et al: "Niemann-Pick type C disease involves disrupted neurosteroidogenesis and responds to allopregnanlone", Nature Medicine Jul. 2004, vol. 10, No. 7, pp. 704-711.
He, Jun, et al: "Allopregnanolone, a progesterone metabolite, enhances behavioral recovery and decreases neuronal loss after traumatic brain injury", Restorative Neurology and Neuroscience 2004, vol. 22, vol. 1, pp. 19-31.
He, Jun, et al: "Progesterone and allopregnanolone reduce inflammatory cytokines after traumatic brain injury", Experimental Neurology 2004, vol. 189, vol. 2, pp. 404-412.
Irwin, Ronald W., et al: "Frontiers in therapeutic development of allopregnanolone for Alzheimer's disease and other neurological disorders", Frontiers in Cellular Neuroscience Jul. 2014, vol. 8, Article 203, pp. 1-19.
Limmroth, Volker, et al: "GABA-A-receptor-mediated effects of progesterone, its ring-A-reduced metabolites and synthetic neuroactive steroids on neurogenic oedema in the rat meninges", British Journal of Pharmacology 1996, vol. 117, No. 1, pp. 99-104.
Robichaud, Malika, et al: "Allopregnanolone and ganaxolone increase the firing activity of dorsal raphe nucleus serotonergic neurons in female rats", International Journal of Neuropsychopharmacology 2006, vol. 9, No. 2, pp. 191-200.
Wang, Jun Ming, et al: "Allpregnanolone reverses neurogenic and cognitive deficits in mouse model of Alzheimer's disease", PNAS Apr. 6, 2010, vol. 107, No. 14, pp. 6498-6503.
Zolkowska et al. (2012) "Anticonvulsant Activity of Intravenous and Intramuscular Allopregnenalone," *American Epilepsy Society*,(Abst. 1.023) [retrieved from http://www.aesnet.org/go/publications/aes-abstracts/abstract-search/mode/display/st/roga . . . ], 2 pages, published to web on Sep. 6, 2012.

\* cited by examiner

Fig. 7

EDIBLE OILS TO ENHANCE DELIVERY OF ORALLY ADMINISTERED STEROIDS

CROSS-REFERENCE TO RELATED APPLICATIONS

This application is a U.S. National Phase under 35 U.S.C. § 371 of Intl. Appl. No. PCT/US2012/056509, filed on Sep. 21, 2012, which claims the benefit under 35 U.S.C. § 119(e) of U.S. Provisional Application No. 61/538,546, filed on Sep. 23, 2011, which are hereby incorporated herein by reference in their entirety for all purposes.

FIELD OF THE INVENTION

The present invention relates to the formulation of steroids, including neurosteroids (e.g., allopregnanolone (ALP)) in edible oils to enhance their absorption when administered, e.g., orally or transmucosally to a patient.

BACKGROUND OF THE INVENTION

Steroids, including neurosteroids (e.g., allopregnanolone) are highly insoluble in aqueous solution. Various approaches are used to enhance aqueous dissolution, including the use of cyclodextrin solutions. However, even with cyclodextrin as a solvation aid, solubility is not sufficient to permit oral delivery for the treatment of medical conditions. Another approach that has been used is nanosizing and coating of nanoparticles, which are then formulated as aqueous suspensions or pills. Nanosizing and coating has been found to enhance absorption and reduce the "food effect" whereby absorption is highly variable and dependent upon dosing with or without a fatty meal. Still, this approach requires large amounts of the steroid to be delivered because of poor bioavailability. There is presently no acceptable approach for the oral delivery of neurosteroids.

SUMMARY OF THE INVENTION

In one aspect, the invention provides compositions comprising a steroid and an edible oil.

In another aspect, the invention provides compositions consisting essentially of a steroid and an edible oil.

In some embodiments, the steroid is a neurosteroid. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the steroid is not progesterone.

In some embodiments, the steroid is suspended or dissolved in the edible oil. In some embodiments, the edible oil comprises one or more a vegetable oils. In some embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof. In some embodiments, the edible oil is canola oil. In some embodiments, the edible oil is peanut oil. In some embodiments, the edible oil comprises one or more a nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof. The edible oil can also comprise a mixture of vegetable oils and nut oils, as appropriate or desired.

In some embodiments, the composition comprises or consists essentially of allopregnanolone and canola oil. In some embodiments, the composition comprises or consists essentially of allopregnanolone and peanut oil.

In some embodiments, the composition is contained within a soft gel capsule for oral delivery to a subject.

In a further aspect, the invention provides methods of treating, reducing, and/or mitigating symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including postpartum depression), premenstrual dysphoric disorder, alcohol craving, and smoking cessation in a subject in need thereof, comprising administration to the subject orally or transmucosally a composition as described above and herein. In some embodiments, the composition is administered orally.

In a related aspect, the invention provides methods of treating, reducing, and/or mitigating symptoms associated with and/or caused by epilepsy, in a subject in need thereof, comprising administration to the subject orally or transmucosally a composition as described above and herein. In a further aspect, the invention provides methods of accelerating the termination or abortion of an impending seizure in a subject in need thereof, comprising administration to the subject orally or transmucosally a composition as described above and herein. In some embodiments, the subject is experiencing aura. In some embodiments, the subject has been warned of an impending seizure. In some embodiments, the subject is experiencing a seizure. In some embodiments, the subject has status epilepticus. In some embodiments, the subject has myoclonic epilepsy. In some embodiments, the subject suffers from seizure clusters. In some embodiments, the seizure is a tonic seizure. In some embodiments, the seizure is a clonic seizure.

Definitions

As used herein, "administering" refers to oral ("po") administration and transmucosal (e.g., oral, nasal, vaginal, rectal, or transdermal) delivery.

The term "co-administration" refers to the presence of both active agents in the blood at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The term "effective amount" or "pharmaceutically effective amount" refer to the amount and/or dosage, and/or dosage regime of one or more compounds necessary to bring about the desired result e.g., an amount sufficient prevent, abort or terminate a seizure.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The terms "reduce," "inhibit," "relieve," "alleviate" refer to the detectable decrease in the frequency, severity and/or duration of seizures. A reduction in the frequency, severity and/or duration of seizures can be measured by self-assessment (e.g., by reporting of the patient) or by a trained clinical observer. Determination of a reduction of the frequency, severity and/or duration of seizures can be made by comparing patient status before and after treatment.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrase "consisting essentially of" refers to the genera or species of active pharmaceutical agents (e.g., neurosteroid, e.g., allopregnanolone) and excipient (e.g., edible oil) included in a method or composition. In various embodiments, other unmentioned or unrecited active ingredients and inactive are expressly excluded. In various embodiments, additives (e.g., surfactants, acids (organic or fatty), alcohols, esters, co-solvents, solubilizers, lipids, polymers, glycols) are expressly excluded.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

The term "edible oil" refers to an oil that is digestible by a mammal. Preferred oils are edible or digestible without inducing undesirable side effects.

The term "neuroactive steroid" or "neurosteroid" refers to steroid compounds that rapidly alter neuronal excitability through interaction with neurotransmitter-gated ion channels. Neurosteroids act as allosteric modulators of neurotransmitter receptors, such as $GABA_A$, NMDA, and sigma receptors. Neurosteroids find use as sedatives for the purpose of general anaesthesia for carrying out surgical procedures, and in the treatment of epilepsy and traumatic brain injury. Illustrative neurosteroids include, e.g., allopregnanolone, Ganaxolone, alphaxolone, alphadolone, hydroxydione, minaxolone, and Althesin (a mixture of alphaxolone and alphadolone).

DETAILED DESCRIPTION

1. Introduction

The present invention is based, in part, on the discovery that edible oils (e.g., including without limitation peanut oil, canola oil, olive oil) markedly enhance the absorption of steroids, including neurosteroids (e.g., allopregnanolone) delivered to a patient via the oral route. Suspending or dissolving steroids in an edible oil presents a practical and efficacious method of administering steroids, including neurosteroids (e.g., allopregnanolone), to a patient. Large concentrations of steroids can be carried in a relatively small volume of oil. Therefore, the volume necessary to deliver an equivalent amount of steroid is much smaller when formulated in an edible oil carrier than when formulated in an aqueous solution carrier (e.g., using a solubilizer cyclodextrin solution). Steroids, and particularly neurosteroids, have poor bioavailability when administered orally. Therefore, large amounts must be administered to achieve satisfactory exposure. It is oftentimes impractical to deliver such large amounts (e.g., because each dose requires many pills or excessively large pills that are difficult to swallow) and the cost of goods may be prohibitive.

Surprisingly, the absorption and delivery to the brain of neurosteroids, including allopregnanolone, can be promoted or increased when the steroid is suspended or dissolved in an edible oil. Formulation in an edible oil allows for the practical and efficacious delivery of steroids, including neurosteroids (e.g., allopregnanolone) orally. In various embodiments, the steroid, including neurosteroids (e.g., allopregnanolone) dissolved or suspended in an edible oil can be administered in a gelatin capsule, e.g., produced by soft-gel encapsulation technology. For example, parenteral administration of allopregnanolone as an aqueous solution in hydroxypropyl-beta-cyclodextrin, readily causes central nervous system effects. By comparison, even high doses of allopregnanolone administered orally in an aqueous solution, such as in an aqueous solution of hydroxyproply-beta-cyclodextrin, failed to produce central nervous system effects. However, allopregnanolone at doses of 250 mg/kg in canola oil, produces profound sedation and anticonvulsant activity in the pentylenetetrazol seizure test, demonstrating that the allopregnanolone formulated in the edible oil is absorbed.

2. Subjects who can Benefit

In various embodiments, the subject has a condition that can be treated or mitigated by administration of a neurosteroid, e.g., allopregnanolone. Allopregnanolone has many medical uses, including the treatment, reduction, and/or mitigation of symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, and smoking cessation. The subject may or may not be exhibiting symptoms.

Accordingly, the invention also contemplates methods of treating, reducing, and/or mitigating symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, and smoking cessation by administration of a steroid or neurosteroid (e.g., allopregnanolone) dissolved or suspended in an edible oil, as described herein.

In some embodiments, the subject has epilepsy, has a history of suffering from epileptic seizures or is suffering from epileptic seizures. In various embodiments, the patient may be experiencing an electrographic or behavioral seizure or may be experiencing a seizure aura, which itself is a localized seizure that may spread and become a full blown behavioral seizure. For example, the subject may be experiencing aura that alerts of the impending onset of a seizure or seizure cluster.

Alternatively, the subject may be using a seizure prediction device that alerts of the impending onset of a seizure or seizure cluster. Implantable seizure prediction devices are known in the art and described, e.g., in D'Alessandro, et al., IEEE TRANSACTIONS ON BIOMEDICAL ENGINEERING, VOL. 50, NO. 5, MAY 2003, and U.S. Patent Publication Nos. 2010/0198098, 2010/0168603, 2009/0062682, and 2008/0243022.

The subject may have a personal or familial history of any of the epileptic conditions described herein. The subject may have been diagnosed as having any of the epileptic conditions described herein. In some embodiments, the subject has or is at risk of suffering a myoclonic seizure or myoclonic epilepsy, e.g., juvenile myoclonic epilepsy. The PTZ seizure model demonstrated herein is predictive of utility and/or activity in counteracting myoclonic seizures or myoclonic epilepsy in humans.

In various embodiments, the subject may be at risk of exposure to or may have been exposed to a nerve agent or a pesticide that can cause seizures. Illustrative nerve agents that can cause seizures include, e.g., organophosphorus nerve agents, e.g., tabun, sarin, soman, GF, VR and/or VX. Illustrative pesticides that can cause seizures include, e.g., organophosphate pesticides (e.g., Acephate (Orthene), Azinphos-methyl (Gusathion, Guthion), Bensulide (Betasan, Lescosan), Bomyl (Swat), Bromophos (Nexion), Bromophos-ethyl (Nexagan), Cadusafos (Apache, Ebufos, Rugby), Carbophenothion (Trithion), Chlorethoxyfos (Fortress), Chlorfenvinphos (Apachlor, Birlane), Chlormephos (Dotan), Chlorphoxim (Baythion-C), Chlorpyrifos (Brodan, Dursban, Lorsban), Chlorthiophos (Celathion), Coumaphos (Asuntol, Co-Ral), Crotoxyphos (Ciodrin, Cypona), Crufomate (Ruelene), Cyanofenphos (Surecide), Cyanophos (Cyanox), Cythioate (Cyflee, Proban), DEF (De-Green), E-Z-Off D), Demeton (Systox), Demeton-S-methyl (Duratox, Metasystoxl), Dialifor (Torak), Diazinon, Dichlorofenthion, (VC-13 Nemacide), Dichlorvos (DDVP, Vapona), Dicrotophos (Bidrin), Dimefos (Hanane, Pestox XIV), Dimethoate (Cygon, DeFend), Dioxathion (Delnav), Disulfoton (Disyston), Ditalimfos, Edifenphos, Endothion, EPBP (S-seven), EPN, Ethion (Ethanox), Ethoprop (Mocap), Ethyl parathion (E605, Parathion, thiophos), Etrimfos (Ekamet), Famphur (Bash, Bo-Ana, Famfos), Fenamiphos (Nemacur), Fenitrothion (Accothion, Agrothion, Sumithion), Fenophosphon (Agritox, trichloronate), Fensulfothion (Dasanit), Fenthion (Baytex, Entex, Tiguvon), Fonofos (Dyfonate, N-2790), Formothion (Anthio), Fosthietan (Nem-A-Tak), Heptenophos (Hostaquick), Hiometon (Ekatin), Hosalone (Zolone), IBP (Kitazin), Iodofenphos (Nuvanol-N), Isazofos (Brace, Miral, Triumph), Isofenphos (Amaze, Oftanol), Isoxathion (E-48, Karphos), Leptophos (Phosvel), Malathion (Cython), Mephosfolan (Cytrolane), Merphos (Easy Off-D, Folex), Methamidophos (Monitor), Methidathion (Supracide, Ultracide), Methyl parathion (E601, Penncap-M), Methyl trithion, Mevinphos (Duraphos, Phosdrin), Mipafox (Isopestox, Pestox XV), Monocrotophos (Azodrin), Naled (Dibrome), Oxydemeton-methyl (Metasystox-R), Oxydeprofos (Metasystox-S), Phencapton (G 28029), Phenthoate (Dimephenthoate, Phenthoate), Phorate (Rampart, Thimet), Phosalone (Azofene, Zolone), Phosfolan (Cylan, Cyolane), Phosmet (Imidan, Prolate), Phosphamidon (Dimecron), Phostebupirim (Aztec), Phoxim (Baythion), Pirimiphos-ethyl (Primicid), Pirimiphos-methyl (Actellic), Profenofos (Curacron), Propetamphos (Safrotin), Propyl thiopyrophosphate (Aspon), Prothoate (Fac), Pyrazophos (Afugan, Curamil), Pyridaphenthion (Ofunack), Quinalphos (Bayrusil), Ronnel (Fenchlorphos, Korlan), Schradan (OMPA), Sulfotep (Bladafum, Dithione, Thiotepp), Sulprofos (Bolstar, Helothion), Temephos (Abate, Abathion), Terbufos (Contraven, Counter), Tetrachlorvinphos (Gardona, Rabon), Tetraethyl pyrophosphate (TEPP), Triazophos (Hostathion), and Trichlorfon (Dipterex, Dylox, Neguvon, Proxol).

3. Steroids

The compositions generally comprise or consist essentially of a steroid, e.g., a neurosteroid, suspended or dissolved in an edible oil.

In various embodiments the neurosteroid is allopregnanolone (ALP). Allopregnanolone, also known as 3α-hydroxy-5α-pregnan-20-one or 3α,5α-tetrahydroprogesterone, IUPAC name 1-(3-Hydroxy-10,13-dimethyl-2,3,4,5,6, 7,8,9,11,12,14,15,16,17-tetradecahydro-1H-cyclopenta[a] phenanthren-17-yl)ethanone, and referenced as CAS number 516-54-1, is a prototypic neurosteroid present in the blood and also the brain. It is a metabolite of progesterone and modulator of $GABA_A$ receptors. While allopregnanolone, like other $GABA_A$ receptor active neurosteroids such as allotetrahydrodeoxycorticosterone (3α,21-dihydroxy-5α-pregnan-20-one; THDOC), positively modulates all $GABA_A$ receptor isoforms, those isoforms containing δ-subunits exhibit greater magnitude potentiation. Allopregnanolone has pharmacological properties similar to other positive modulators of $GABA_A$ receptors, including anxiolytic and anticonvulsant activity. Allopregnanolone is neuroprotective in many animal models of neurodegenerative conditions, including, e.g., Alzheimer's disease (Wang et al., *Proc Natl Acad Sci USA*. 2010 Apr. 6; 107(14):6498-503), cerebral edema (Limmroth et al., *Br J Pharmacol*. 1996

January; 117(1):99-104) and traumatic brain injury (He et al., *Restor Neurol Neurosci.* 2004; 22(1):19-31; and He, et al., *Exp Neurol.* 2004 October; 189(2):404-12), Mood disorders (Robichaud and Debonnel, *Int J Neuropsychopharmacol.* 2006 April; 9(2):191-200), Niemann-Pick type C disease (Griffin et al., *Nat Med.* 2004 July; 10(7):704-11) and acts as an anticonvulsant against chemically induced seizures, including the pentylenetetrazol (PTZ) model (Kokate et al., *J Pharmacol Exp Ther.* 1994 September; 270(3):1223-9). The chemical structure of allopregnanolone is depicted below in Formula I:

In various embodiments, the compositions comprise a sulfate, salt, hemisuccinate, nitrosylated, derivative or congener of allopregnanolone.

Delivery of other neurosteroids also can be enhanced by formulation in an edible oil. Other neurosteroids that can be formulated in an edible oil, include without limitation allotetrahydrodeoxycorticosterone (3α,21-dihydroxy-5α-pregnan-20-one; THDOC), 3α,21-dihydroxy-5b-pregnan-20-one, pregnanolone (3α-hydroxy-5β-pregnan-20-one), Ganaxolone (INN, also known as CCD-1042; IUPAC name (3α,5α)-3-hydroxy-5-methylpregnan-20-one; 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethanone), alphaxolone, alphadolone, hydroxydione, minaxolone, and Althesin (a mixture of alphaxolone, alphadolone, tetrahydrodeoxycorticosterone, pregnenolone, dehydroepiandrosterone (DHEA), 7-substituted benz[e]indene-3-carbonitriles (see, e.g., Hu, et al., *J Med Chem.* (1993) 36(24):3956-67); 7-(2-hydroxyethyl) benz[e]indene analogues (see, e.g., Han, et al., *J Med Chem.* (1995) 38(22):4548-56); 3 alpha-hydroxy-5 alpha-pregnan-20-one and 3 alpha-hydroxy-5 beta-pregnan-20-one analogues (see, e.g., Han, et al., *J Med Chem.* (1996) 39(21): 4218-32); enantiomers of dehydroepiandrosterone sulfate, pregnenolone sulfate, and (3alpha,5beta)-3-hydroxypregnan-20-one sulfate (see, e.g., Nilsson, et al., *J Med Chem.* (1998) 41(14):2604-13); 13,24-cyclo-18,21-dinorcholane analogues (see, e.g., Jiang, et al., *J Med Chem.* (2003) 46(25):5334-48); N-acylated 17a-aza-D-homosteroid analogues (see, e.g., Covey, et al., *J Med Chem.* (2000) 43(17): 3201-4); 5 beta-methyl-3-ketosteroid analogues (see, e.g., Zeng, et al., *J Org Chem.* (2000) 65(7):2264-6); 18-norandrostan-17-one analogues (see, e.g., Jiang, et al., *J Org Chem.* (2000) 65(11):3555-7); (3alpha,5alpha)- and (3alpha,5beta)-3-hydroxypregnan-20-one analogs (see, e.g., Zeng, et al., *J Med Chem.* (2005) 48(8):3051-9); benz[f]indenes (see, e.g., Scaglione, et al., *J Med Chem.* (2006) 49(15):4595-605); enantiomers of androgens (see, e.g., Katona, et al., *Eur J Med Chem.* (2008) 43(1):107-13); cyclopenta[b]phenanthrenes and cyclopenta[b]anthracenes (see, e.g., Scaglione, et al., *J Med Chem.* (2008) 51(5):1309-18); 2beta-hydroxygonane derivatives (see, e.g., Wang, et al., *Tetrahedron* (2007) 63(33):7977-7984); Δ16-alphaxalone and corresponding 17-carbonitrile analogues (see, e.g., Bandyopadhyaya, et al., *Bioorg Med Chem Lett.* (2010) 20(22):6680-4); Δ(16) and Δ(17(20)) analogues of Δ(16)-alphaxalone (see, e.g., Stastna, et al., *J Med Chem.* (2011) 54(11):3926-34); neurosteroid analogs developed by CoCensys (now Purdue Neuroscience) (e.g., CCD-3693, Co2-6749 (a.k.a., GMA-839 and WAY-141839); neurosteroid analogs described in U.S. Pat. No. 7,781,421 and in PCT Patent Publications WO 2008/157460; WO 1993/003732; WO 1993/018053; WO 1994/027608; WO 1995/021617; WO 1996/016076; WO 1996/040043, as well as salts, hemisuccinates, nitrosylated, sulfates and derivatives thereof.

In various embodiments, the steroid or neurosteroid is not a sex hormone. In various embodiments, the steroid or neurosteroid is not progesterone.

As appropriate, the steroid or neurosteroid (e.g., allopregnanolone) may or may not be micronized. As appropriate, the steroid or neurosteroid (e.g., allopregnanolone) may or may not be enclosed in microspheres in suspension in the oil.

4. Edible Oils

The steroid or neurosteroid is dissolved or suspended in an oil that is edible and/or digestible by the subject, e.g., without undesirable side effects.

In various embodiments, the edible oil comprises one or more vegetable oils. In various embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof.

In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof.

In some embodiments, the edible oil does not comprise castor oil. In some embodiments, the edible oil does not comprise peanut oil.

Generally, the oils used in the present compositions are isolated from the source, e.g., plant, and used without including further additives (e.g., surfactants, acids (organic or fatty), alcohols, esters, co-solvents, solubilizers, lipids, polymers, glycols) or processing. In various embodiments, the oil vehicle further comprises a preservative (e.g., vitamin E).

5. Formulation and Administration

The oil-steroid compositions can be formulated for oral and/or transmucosal delivery using any method known in the art. In one embodiment, the oil-steroid composition is formulated in a capsule, e.g., for oral delivery.

a. Capsules

The capsule shells can be prepared using one or more film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose, hydroxypropyl methyl cellulose acetate succinate, hydroxypropyl methyl cellulose phthalate, and cellulose acetate phthalate. Hard or soft capsules can be used to administer the hormone. Hard shell capsules are typically prepared by forming the two capsule halves, filling one of the halves with the fill solution, and then sealing the capsule halves together to form the finished capsule. Soft gelatin capsules are typically prepared using a rotary die encapsulation process as described below.

i. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid-processed gelatins form stronger gels than lime-processed gelatins of the same average molecular weight. The capsules can be formulated as hard or soft gelatin capsules.

ii. Non-Gelatin Capsules

Capsules can be prepared from non-gelatin materials, such as carrageenan or modified celluloses. Carrageenan is a natural polysaccharide hydrocolloid, which is derived from seaweed. It includes a linear carbohydrate polymer of repeating sugar units, without a significant degree of substitution or branching. Most, if not all, of the galactose units on a carrageenan molecule possess a sulfate ester group. There are three main types of carrageenan: kappa, iota and lambda; although minor forms called mu and nu carrageenan also exist.

iii. Shell Additives

Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

b. Enteric Capsules

Alternatively, the liquid fills can be incorporated into an enteric capsule, wherein the enteric polymer is a component of the capsule shell, as described in WO 2004/030658 to Banner Pharmacaps, Inc. The enteric capsule shell is prepared from a mass comprising a film-forming polymer, an acid-insoluble polymer which is present in an amount making the capsule resistant to the acid within the stomach, an aqueous solvent, and optionally, one or more plasticizers and/or colorants. Other suitable shell additives including opacifiers, colorants, humectants, preservatives, flavorings, and buffering salts and acids may be added.

i. Film-Forming Polymers

Exemplary film-forming polymers can be of natural or synthetic origin. Natural film-forming polymers include gelatin and gelatin-like polymers. Other suitable natural film-forming polymers include shellac, alginates, pectin, and zeins. Synthetic film-forming polymers include hydroxypropyl methyl cellulose, methyl cellulose, hydroxypropyl methyl cellulose acetate succinate, hydroxypropyl methyl cellulose phthalate, cellulose acetate phthalate, and acrylates such as poly (meth)acrylate. The weight ratio of acid-insoluble polymer to film-forming polymer is from about 15% to about 50%. In one embodiment, the film forming polymer is gelatin.

ii. Acid-Insoluble Polymers

Exemplary acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (available under the tradename EUDRAGIT® from Rohm America Inc., Piscataway, N.J. as a powder or a 30% aqueous dispersion; or under the tradename EASTACRYL®, from Eastman Chemical Co., Kingsport, Tenn., as a 30% dispersion). In one embodiment, the acid-insoluble polymer is EUDRAGIT® L100, which is a methacrylic acid/methacrylic acid methyl ester copolymer. The acid-insoluble polymer is present in an amount from about 8% to about 20% by weight of the wet gelatin mass. The weight ratio of acid-insoluble polymer to film-forming polymer is from about 15% to about 50%.

iii. Aqueous Solvent

Hard and soft capsules are typically prepared from solutions or suspensions of the film forming polymer and the acid-insoluble polymer. Suitable solvents include water, aqueous solvents, and organic solvents. In one embodiment, the solvent is water or an aqueous solvent. Exemplary aqueous solvents include water or aqueous solutions of alkalis such as ammonia, sodium hydroxide, potassium hydroxide, ethylene diamine, hydroxylamine, tri-ethanol amine, or hydroalcoholic solutions of the same. The alkali can be adjusted such that the final pH of the gelatin mass is less than or equal to 9.0, preferably less than or equal to 8.5, more preferably less than or equal to 8.0. In one embodiment, the alkali is a volatile alkali such as ammonia or ethylene diamine. Upon drying of the finished capsule, the water content of the capsule is from about 2% to about 10% by weight of the capsule, preferably from about 4% to about 8% by weight of the capsule.

iv. Plasticizers

Exemplary plasticizers include glycerol, glycerin, sorbitol, polyethylene glycol, citric acid, citric acid esters such as triethylcitrate, polyalcohols with 3-6 carbons and combinations thereof. The plasticizer to polymer (film forming polymer plus acid-insoluble polymer) ratio is from about 10% to about 50% of the polymer weight.

c. Methods of Manufacture i. Capsule Fill

The fill material is prepared by dissolving the steroid or neurosteroid (e.g., allopregnanolone) in the carrier containing a fatty acid solvent, such as oleic acid. The mixture of hormone and fatty acid may be heated to facilitate dissolution of the hormone. Upon cooling to room temperature and encapsulation, the solution remains a liquid. The fill is typically deaerated prior to encapsulation in a soft gelatin capsule. Additional excipients including, but not limited to, co-solvents, antioxidants may be added to the mixture of the hormone and fatty acid. Again the mixture may be heated to facilitate dissolution of the excipients. The steroid or neurosteroid (e.g., allopregnanolone) is fully dissolved in the carrier of the present invention and remains so upon storage.

i. Capsule Shell a. Gelatin or Non-Gelatin Capsules

The main ingredients of the capsule shell are gelatin (or a gelatin substitute for non-gelatin capsules), plasticizer, and purified water. The primary difference between soft and hard capsules is the amount of plasticizer present in the capsule shell.

Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt or a hot melt process. The prepared gel masses are transferred to preheated, temperature-controlled, jacketed holding tanks where the gel mass is aged at 50-60° C. until used for encapsulation.

i. Cold Melt Process

The cold melt process involves mixing gelatin with plasticizer and chilled water and then transferring the mixture to a jacket-heated tank. Typically, gelatin is added to the plasticizer at ambient temperature (18-22° C.). The mixture is cooked (57-95° C.) under vacuum for 15-30 minutes to a homogeneous, deaerated gel mass. Additional shell additives can be added to the gel mass at any point during the gel manufacturing process or they may be incorporated into the finished gel mass using a high torque mixer.

ii. Hot Melt Process

The hot melt process involves adding, under mild agitation, the gelatin to a preheated (60-80° C.) mixture of plasticizer and water and stirring the blend until complete melting is achieved. While the hot melt process is faster than the cold melt process, it is less accurately controlled and more susceptible to foaming and dusting.

b. Soft Capsules

Soft capsules are typically produced using a rotary die encapsulation process. The gel mass is fed either by gravity or through positive displacement pumping to two heated (48-65° C.) metering devices. The metering devices control the flow of gel into cooled (10-18° C.), rotating casting drums. Ribbons are formed as the cast gel masses set on contact with the surface of the drums.

The ribbons are fed through a series of guide rolls and between injection wedges and the capsule-forming dies. A food-grade lubricant oil is applied onto the ribbons to reduce their tackiness and facilitate their transfer. Suitable lubricants include mineral oil, medium chain triglycerides, and soybean oil. Fill formulations are fed into the encapsulation machine by gravity. In the preferred embodiment, the soft capsules contain printing on the surface, optionally identifying the encapsulated agent and/or dosage.

Upon drying of the finished capsule, the water content of the capsule is from about 2% to about 10% by weight of the capsule, preferably from about 4% to about 8% by weight of the capsule.

c. Enteric Capsules

A method of making an enteric capsule shell is described in WO 2004/030658 to Banner Pharmacaps, Inc. The enteric mass is typically manufactured by preparing an aqueous solution comprising a film-forming, water soluble polymer and an acid-insoluble polymer and mixing the solution with one or more appropriate plasticizers to form a gelatin mass. Alternatively, the enteric mass can be prepared by using a ready-made aqueous dispersion of the acid-insoluble polymer by adding alkaline materials such as ammonium, sodium, or potassium hydroxides or other alkalis that will cause the acid-insoluble polymer to dissolve. The plasticizer-wetted, film-forming polymer can then be mixed with the solution of the acid-insoluble polymer. The mass can also be prepared by dissolving the acid-insoluble polymer or polymers in the form of salts of the above-mentioned bases or alkalis directly in water and mixing the solution with the plasticizer-wetted, film-forming polymer. The mass is cast into films or ribbons using heat controlled drums or surfaces. The fill material is encapsulated in a soft capsule using a rotary die. The capsules are dried under controlled conditions of temperature and humidity. The final moisture content of the shell composition is from about 2% to about 10% by weight of the capsule shell, preferably from about 4% to about 8% by weight by weight of the capsule shell.

Alternatively, release of the steroid or neurosteroid (e.g., allopregnanolone) from the capsule can be modified by coating the capsule with one or more modified release coatings, such as sustained release coatings, delayed release coatings, and combinations thereof.

The concentration of the steroid or neurosteroid (e.g., allopregnanolone) in the edible oil vehicle is preferably in unit dosage form. The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

Determination of an effective amount for administration in a single dosage is well within the capability of those skilled in the art, especially in light of the detailed disclosure provided herein. Generally, an efficacious or effective amount of the steroid or neurosteroid (e.g., allopregnanolone) is determined by first administering a low dose or small amount of the agent and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 12th Edition, 2010, supra; in a Physicians' Desk Reference (PDR), 65$^{th}$ Edition, 2011; in *Remington: The Science and Practice of Pharmacy*, 21$^{st}$ Ed., 2005, supra; and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference. In various embodiments, the compositions are formulated for administration of about 5 mg/kg to about 50 mg/kg of the steroid or neurosteroid (e.g., allopregnanolone), e.g., about 5 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

6. Monitoring Efficacy

In various embodiments, administration of a steroid or neurosteroid (e.g., allopregnanolone) to a subject results in the prevention or mitigation of one or more symptoms of the disease condition being treated (e.g., traumatic brain injury, Alzheimer's disease, epilepsy, anxiety, fragile X syndrome, post-traumatic stress disorder, lysosomal storage disorders (Niemann-Pick type C disease), depression (including postpartum depression), premenstrual dysphoric disorder, alcohol craving, and smoking cessation). Symptoms of disease can be compared before and after administration of a steroid or neurosteroid (e.g., allopregnanolone) to the subject. Administration of the steroid or neurosteroid (e.g., allopregnanolone) to the subject is considered to be effective if the symptoms no longer occur after administration (e.g., seizures), or if the symptoms are reduced, alleviated and/or mitigated after administration.

In various embodiments, administration of a steroid or neurosteroid (e.g., allopregnanolone) to a subject results in the prevention of the occurrence of an impending seizure and/or the termination or abortion of a seizure in progress.

In various embodiments, efficacy can be monitored by the subject. For example, in a subject experiencing aura or receiving a warning from a seizure prediction device, the subject can self-administer a dose of the steroid or neurosteroid (e.g., allopregnanolone). If the steroid or neurosteroid (e.g., allopregnanolone) is administered in an efficacious amount, the sensation of aura should subside and/or the seizure prediction device should no longer predict the imminent occurrence of an impending seizure. If the sensation of aura does not subside and/or the seizure prediction device continues to predict an impending seizure, a second dose of steroid or neurosteroid (e.g., allopregnanolone) can be administered.

In other embodiments, the efficacy is monitored by a caregiver. For example, in a subject experiencing the onset of a seizure or in situations where a seizure has commenced, the subject may require administration of the steroid or neurosteroid (e.g., allopregnanolone) by a caregiver. If the steroid or neurosteroid (e.g., allopregnanolone) is administered in an efficacious amount, the seizure, along with the subject's symptoms of the seizure, should terminate or abort. If the seizure does not terminate, a second dose of the steroid or neurosteroid (e.g., allopregnanolone) can be administered.

EXAMPLES

The following examples are offered to illustrate, but not to limit the claimed invention.

Example 1

NIH Swiss mice were fasted 2 hours prior to experiment participation. Allopregnanolone (ALP) was suspended in vehicle (Tween 80 or canola oil). The time point of maximal effect of ALP was established by gavaging ALP and scoring relevant behavioral parameters outlined in the Irwin Test. See, Sylvain Roux, et al., *Current Protocols in Pharmacology*, Unit Number: UNIT 10.10, DOI: 10.1002/0471141755.ph1010s27 Online Posting Date: January, 2005. Lethality, convulsion, tremor, Straub, abnormal gait, fear, sedation, reactivity to touch, loss of traction, loss of righting reflex were measured.

Anticonvulsant potential of ALP was determined with PTZ seizure challenge. Oral gavage various ALP concentrations at 50 µl/10 g body weight, t=−45 min or t=−90 min, 80 mg/kg PTZ s.c. at t=0. Observe 30 min for seizure protection (absence of clonic spasms).

Example 2

Methods

Animals. Male NIH Swiss mice (22-30 g) were housed four per cage. Animals were kept in a vivarium under controlled laboratory conditions (temperature, 22-26° C.; humidity, 40-50%) with an artificial 12-h light/dark cycle and free access to food and water. Animals were allowed to acclimate to the vivarium for ≥5 days. The experiments were performed during the light phase of the light/dark cycle after a ≥30-min period of acclimation to the experimental room. Animals were maintained in facilities fully accredited by the Association for Assessment and Accreditation of Laboratory Animal Care, and all studies were performed under protocols approved by the University of California, Davis, Institutional Animal Care and Use Committee the Animal Care and Use in strict compliance with the Guide for the Care and Use of Laboratory Animals of the National Research Council (National Academy Press, Washington, D.C.; on the internet at nap.edu/readingroom/books/labrats/).

Test substances and drug administration. Solutions of allopreganolone (SAFC Pharma, Madison, Wis., U.S.A.) were made in miglyol (Neobee M5®, Spectrum Chemicals, Gardena, Calif.), canola oil (ConAgra Foods, Omaha, Nebr.) or peanut oil (Sigma-Aldrich, St. Louis, Mo.). The convulsant agent pentylenetetrazol (PTZ) (Sigma-Aldrich, St. Louis, Mo.) was dissolved in saline immediately before use and administered intravenously (i.v.). For the PTZ threshold test, allopregnanolone solutions were administered orally (p.o.) 30 min, 1 hr and 2 hr before PTZ infusion, in a volume equaling 10 ml/kg. For the 6-Hz seizure test, solutions of allopregnanolone in canola oil were administered in a volume equaling 20 ml/kg.

PTZ seizure threshold test. The threshold for various behavioral seizure stages induced by the GABA receptor antagonist PTZ, was determined by infusing PTZ via a 27-gauge, 0.75-inch "butterfly" needle inserted into the lateral tail vein. The needle was secured to the tail vein by a narrow piece of adhesive tape, and the animal was permitted to move freely inside an inverted plastic container with free aeration from the top. PTZ (10 mg/ml) were infused at a constant rate of 0.5 ml/min using a 1-ml syringe (BD Biosciences, Franklin Lakes, N.J.) mounted on a Harvard infusion pump (Harvard Apparatus Inc., Holliston, Mass.). The syringe was connected to the needle by polyethylene tubing. The infusion was stopped at 3 min or at the onset of tonic extension, whichever occurred first. The thresholds to the onset of tonic hindlimb extension were determined by measuring the latency from the start of convulsant infusion to the onset of all the response. The threshold value (milligrams per kilogram) was determined according to the following formula: (infusion duration [seconds]×infusion rate [milliliters per minute]×convulsant drug concentration [milligrams per milliliter]×1000)/(60 s×weight of mouse [grams]).

6-Hz seizure test. Mice were tested with a 3-s corneal stimulus (200-µs duration, 32-mA monopolar rectangular pulses at 6 Hz) delivered by a constant-current device (ECT Unit 5780; Ugo Basile, Comerio, Italy). Ocular anesthetic (0.5% tetracaine) was applied to the corneas 15 min before stimulation. Immediately before stimulation, the corneal electrodes were wetted with saline to provide good electrical contact. The seizures were often preceded by a period of intense locomotor agitation (wild running and jumping). The animals then exhibited a "stunned" posture associated with rearing (bipedal standing), forelimb automatic movements and clonus, twitching of the vibrissae, and Straub-tail. The duration of the seizure activity ranged from 60 to 120 s in untreated animals. Animals resumed their normal exploratory behavior after the seizure. Animals were scored as protected or not protected. An animal was considered protected if it resumed its normal exploratory behavior within 10 s of stimulation.

DISCUSSION

Figure 1:
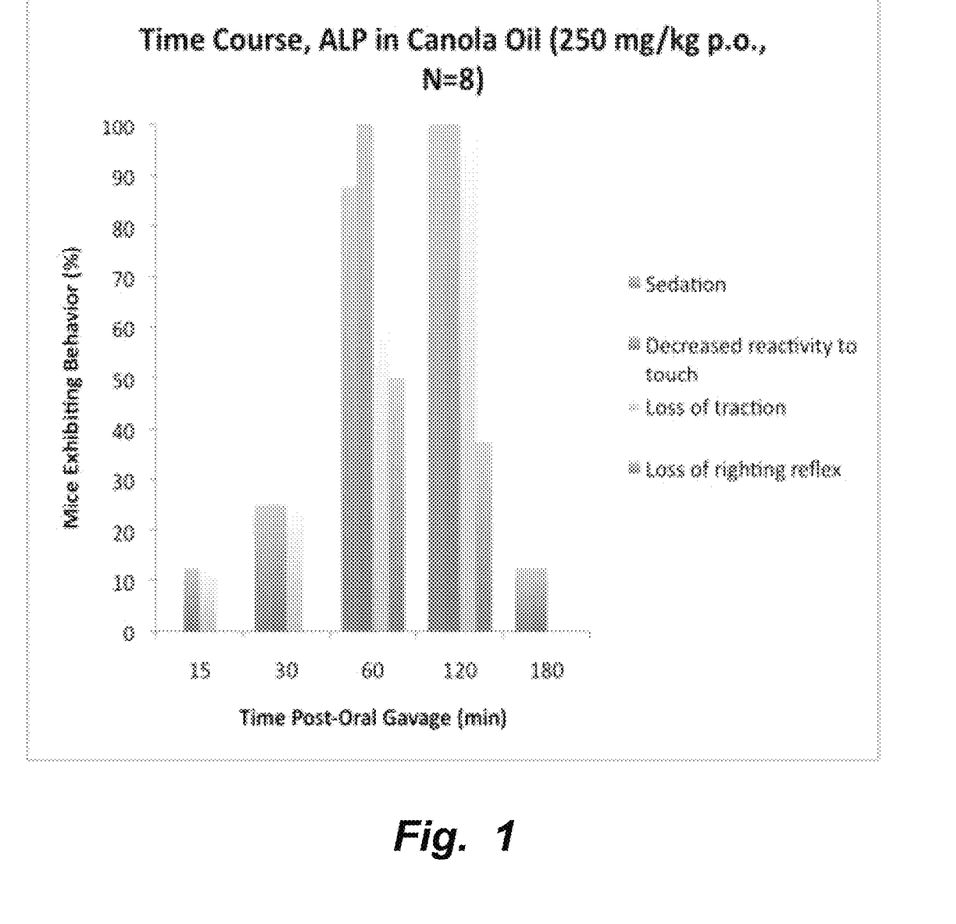
FIG. 1 illustrates time course of allopregnanolone (ALP) activity when administered in a canola oil vehicle to mice by oral gavage.
Figure 2:
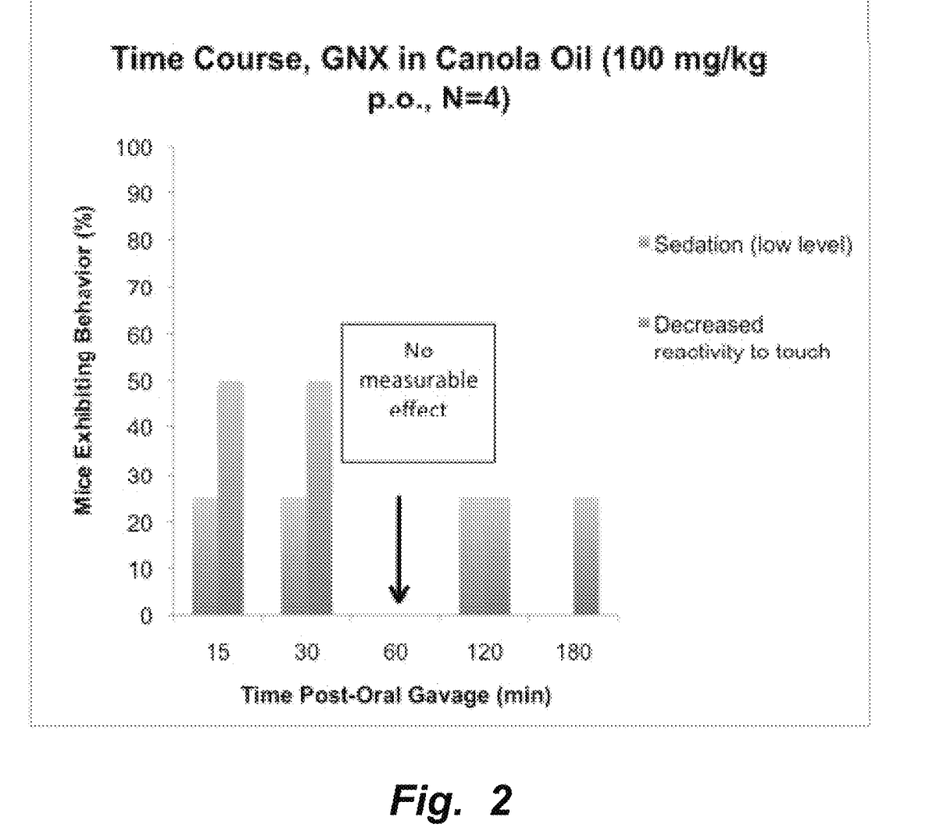
FIG. 2 illustrates time course of ganaxolone (GNX) activity when administered in a canola oil vehicle to mice by oral gavage.
Figure 3:
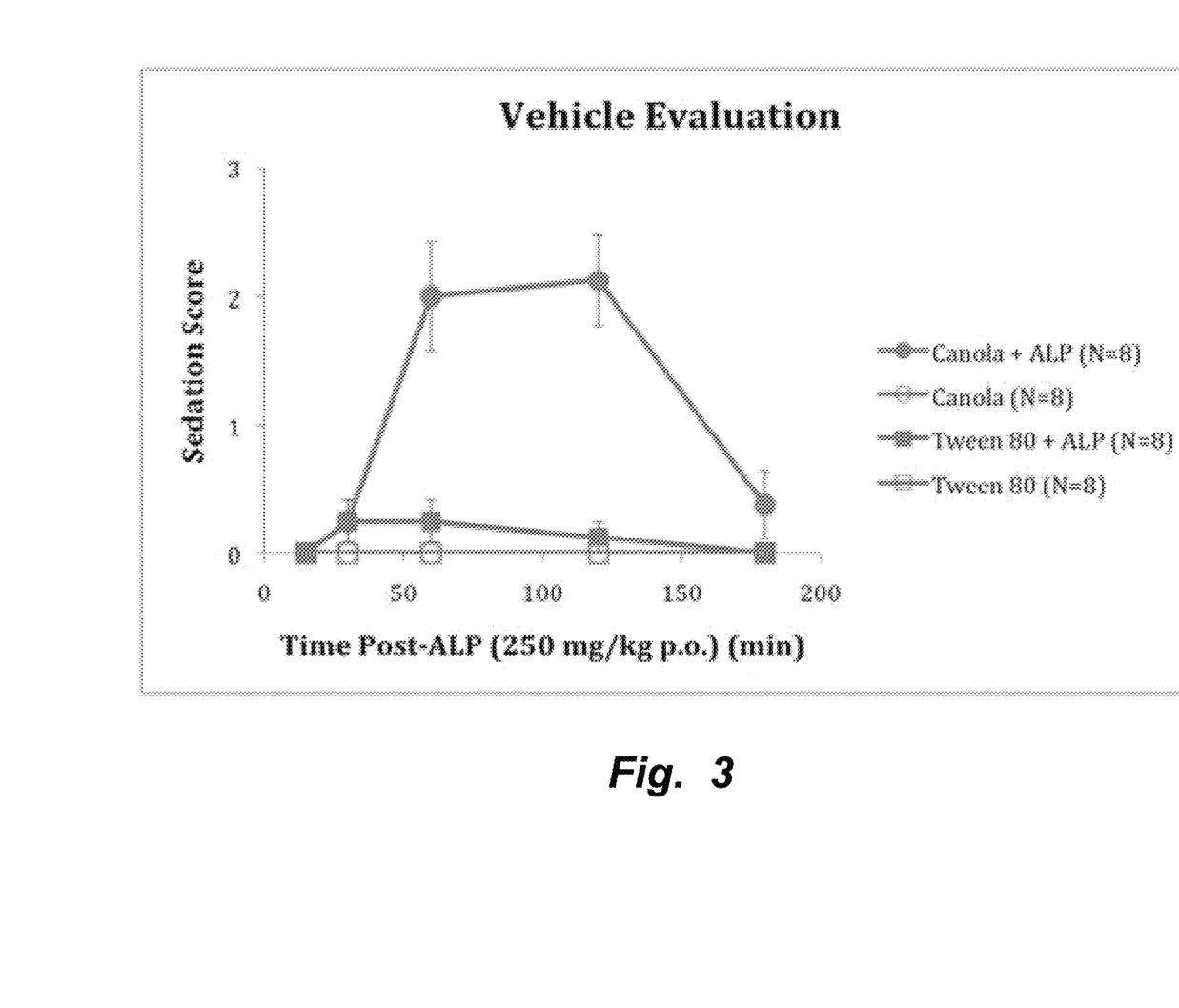
FIG. 3 illustrates a comparison of sedation activity of ALP administered to mice in a canola oil vehicle versus ALP administered to mice in a Tween-80 vehicle.
Figure 4:
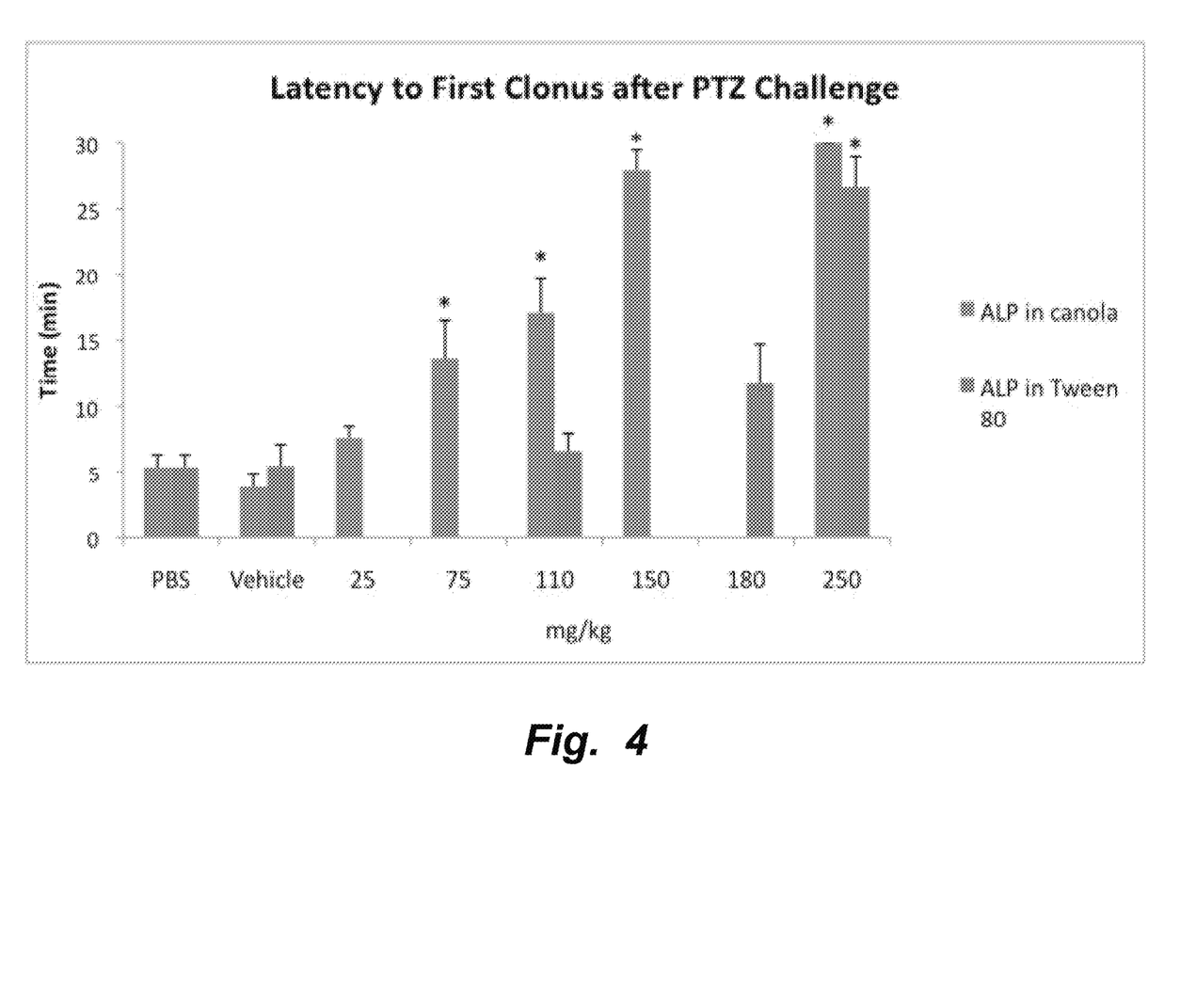
FIG. 4 illustrates that oral delivery of allopregnanolone in canola oil markedly enhances the oral bioavailability of allopregnanolone. This experiment presents a practical approach developed for oral delivery of allopregnanolone. The effective threshold dose was between 25-75 mg/kg. This is a practical dose.
Figure 5:
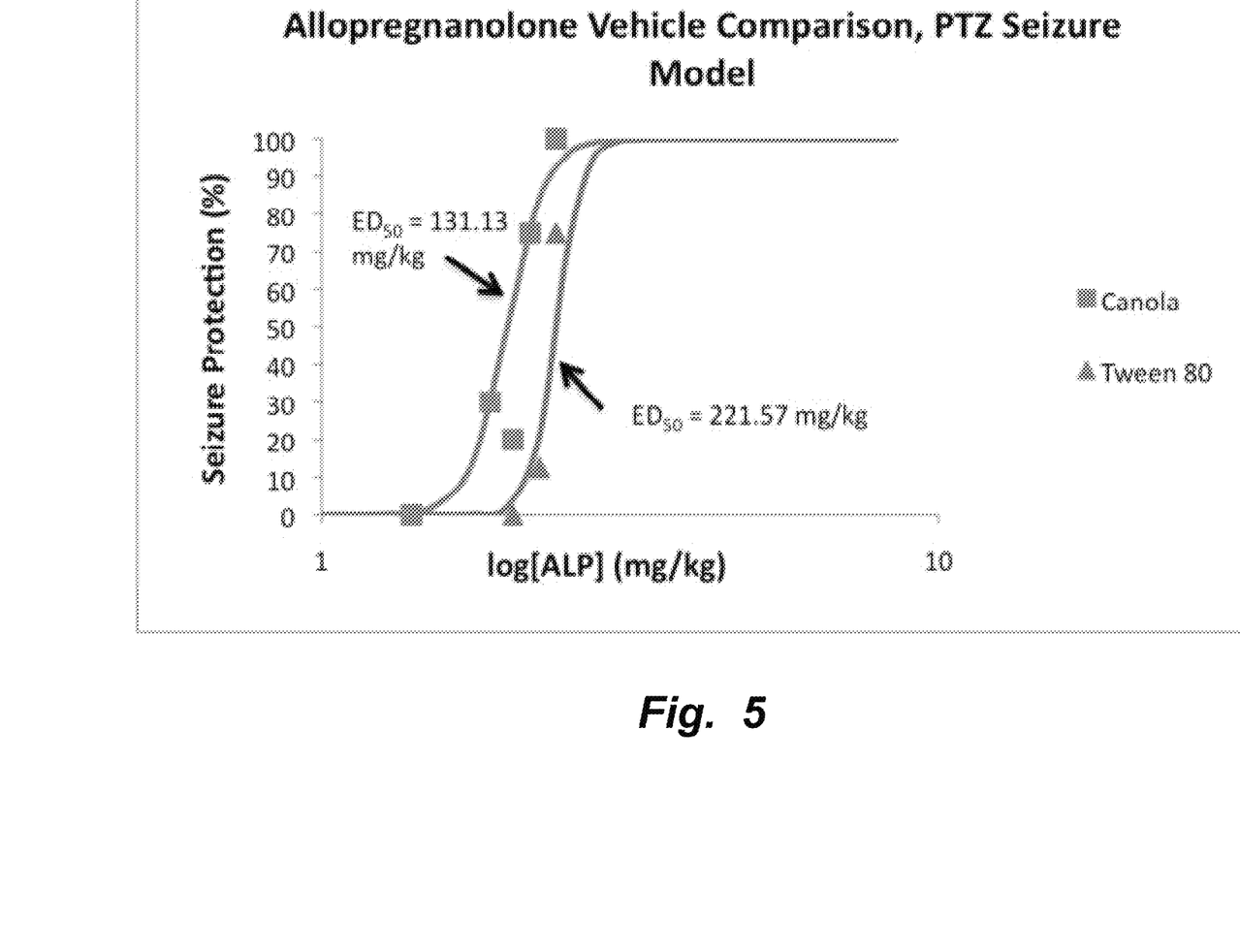
FIG. 5 illustrates a vehicle comparison for anticonvulsant activity of ALP orally delivered in a canola oil vehicle versus ALP administered to mice in a Tween-80 vehicle.
Figure 6:
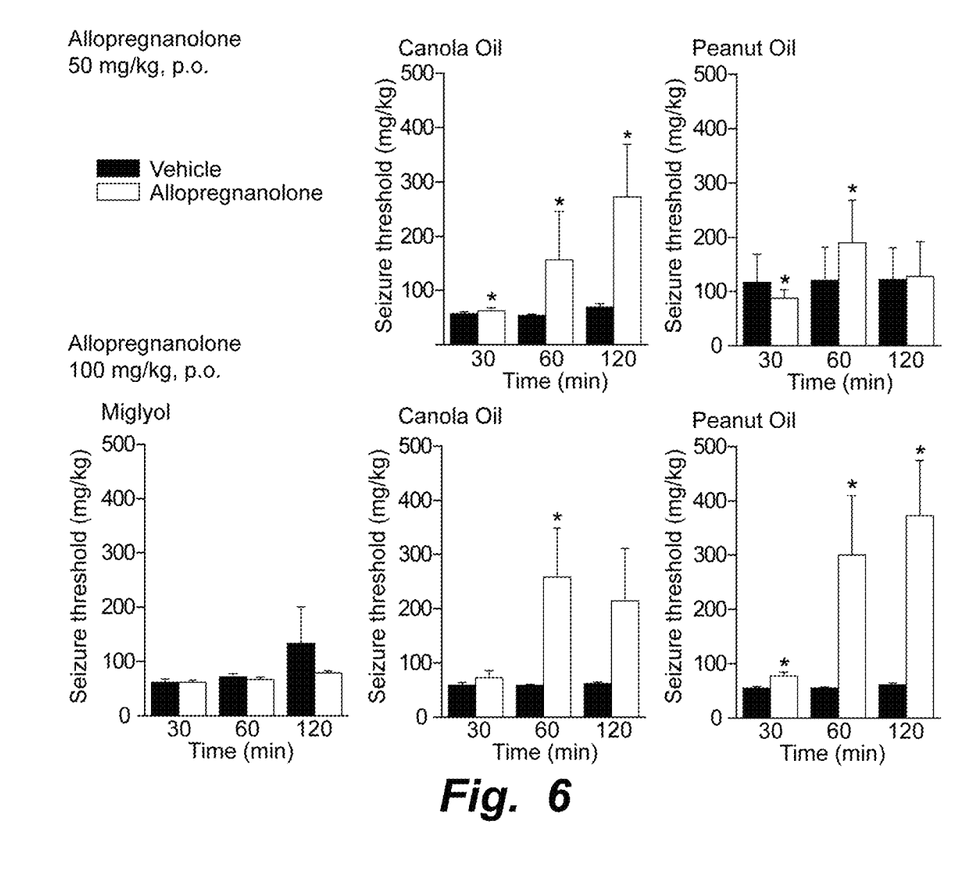
FIG. 6 illustrates a comparison the anticonvulsant activity of orally administered allopregnanolone solubilized by three different oils in the PTZ seizure threshold test. Allopregnanolone dissolved in miglyol was inactive at a dose of 100 mg/kg. In contrast, when dissolved in either canola oil or peanut oil, allopregnanolone at doses of 50 mg/kg (5 mg/ml) and 100 mg/kg (10 mg/ml) caused a time-dependent increase in seizure threshold. The abscissa indicates the time between oral dosing of allopregnanolone or vehicle and the onset of the intravenous PTZ infusion. Each bar represents the mean±S.E.M. of the threshold values for 6-9 mice. *, $p<0.05$ compared with vehicle-treated control group (t-test).
Figure 7:
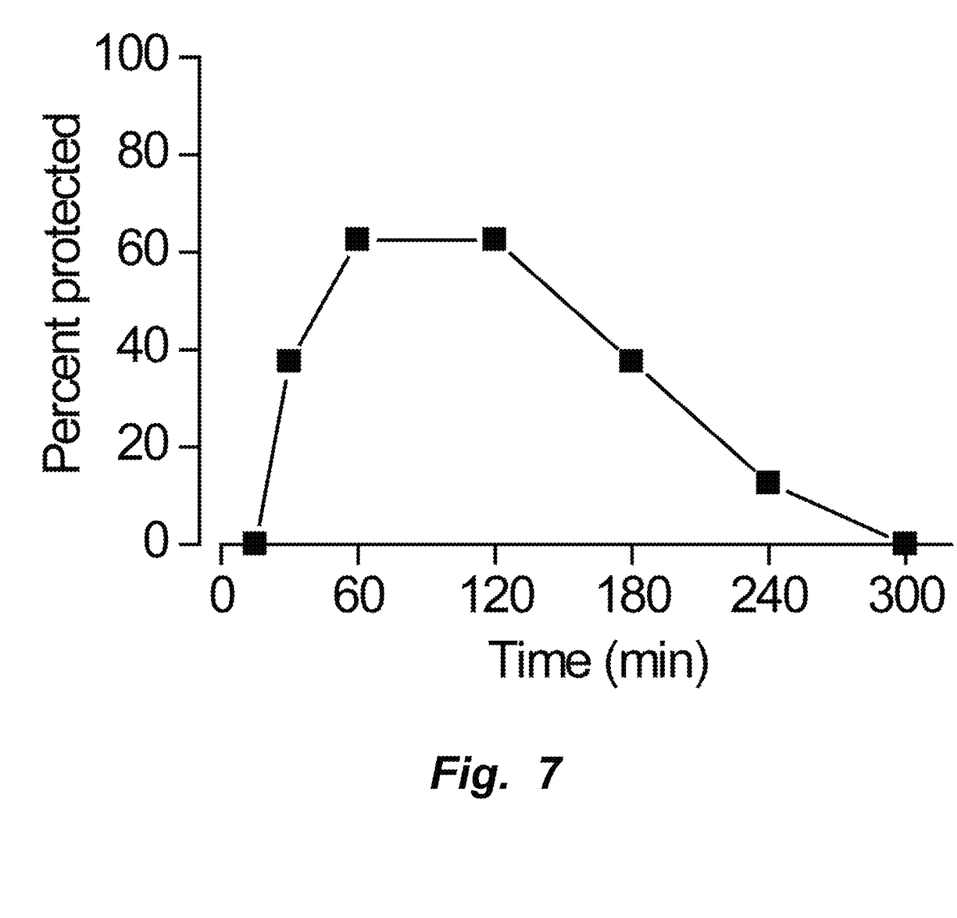
FIG. 7 illustrates a time course for seizure protection in the 6-Hz test produced by allopregnanolone (200 mg/kg) dissolved in canola oil (10 mg/ml). The 6-Hz electrical stimulation was delivered at 32 mA for 3 s. The interval between the steroid injection and the electrical stimulus is plotted on the abscissa and the percentage of animals protected against seizures is plotted on the ordinate. Each point represents 8 mice.

There are many potential clinical applications of the neurosteroid allopregnanolone. For some of these applications, the preferred route of administration is by mouth. However, absorption of orally administered allopregnanolone is poor so that oral administration is not practical. A method to overcome this limitation has been discovered. Allopregnanolone was found to readily dissolve in three oils. When dissolved in miglyol, allopregnanolone exhibited no bioactivity in the PTZ seizure threshold test. Surprisingly, however, when dissolved in canola oil or peanut oil, activity was obtained in the PTZ seizure threshold test. Allopregnanolone dissolved in canola oil also had activity in the 6-Hz seizure test. Allopregnanolone dissolved in canola oil or peanut oil had no or only minimal activity 30 min after administration but had strong activity at 60 min after administration and in some cases activity was also present 120 to 240 min after administration.

These results confirm that allopregnanolone has anti-seizure activity. Dissolving allopregnanolone in canola oil and peanut oil provides a practical method to deliver the neurosteroid by the oral route. When dissolved in these oils, allopregnanolone confers long-lasting anti-seizure activity. Surprisingly, allopregnanolone was highly activity only when dissolved in canola oil and peanut oil; no activity was obtained when the neurosteroid was dissolved in miglyol. The discovery of activity with solutions in canola oil and peanut oil is unexpected.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating, reducing, and/or mitigating a seizure caused by epilepsy, in a subject in need thereof, comprising administration to the subject orally a therapeutic regimen comprising a composition comprising allopregnanolone formulated in an edible oil selected from the group consisting of canola oil, peanut oil, and mixtures thereof, wherein the composition does not comprise a surfactant, wherein the subject suffers from seizure clusters, and wherein the allopregnanolone is administered at a dose from about 50 mg/kg to about 250 mg/kg.

2. The method of claim 1, wherein the composition consists essentially of allopregnanolone and the edible oil.

3. The method of claim 1, wherein the allopregnanolone is suspended or dissolved in the edible oil.

4. The method of claim 1, wherein the composition is contained within a soft gel capsule for oral delivery to a subject.

5. The method of claim 1, wherein the composition consists essentially of allopregnanolone and canola oil.

6. The method of claim 1, wherein the allopregnanolone is administered at a dose of about 50 mg/kg, 75 mg/kg, 100 mg/kg, 200 mg/kg or 250 mg/kg.

7. A method of reducing the frequency, severity and/or duration of seizures caused by epilepsy, in a subject in need thereof, comprising administration to the subject orally a therapeutic regimen comprising a composition comprising allopregnanolone and an edible oil selected from the group consisting of canola oil, peanut oil, and mixtures thereof, wherein the composition does not comprise a surfactant, wherein the subject suffers from seizure clusters, and wherein the allopregnanolone is administered at a dose from about 50 mg/kg to about 250 mg/kg.

8. The method of claim 7, wherein the subject is experiencing aura.

9. The method of claim 7, wherein the composition consists essentially of allopregnanolone and the edible oil.

10. The method of claim 7, wherein the allopregnanolone is suspended or dissolved in the edible oil.

11. The method of claim 7, wherein the composition is contained within a soft gel capsule for oral delivery to a subject.

12. The method of claim 7, wherein the composition consists essentially of allopregnanolone and canola oil.

13. The method of claim 7, wherein the allopregnanolone is administered at a dose of about 50 mg/kg, 75 mg/kg 100 mg/kg, 200 mg/kg or 250 mg/kg.

14. The method of claim 7, wherein the subject is a human.

15. The method of claim 1, wherein the oral administration of allopregnanolone reduces the frequency, severity and/or duration of seizures caused by epilepsy.

16. The method of claim 1, wherein the subject is a human.

* * * * *